US012773264B2

(12) United States Patent
Stewart et al.

(10) Patent No.: US 12,773,264 B2
(45) Date of Patent: Oct. 27, 2026

(54) DIRECTED PULSED ELECTRIC FIELD ABLATION

(71) Applicant: Medtronic, Inc., Minneapolis, MN (US)

(72) Inventors: Mark T. Stewart, Lino Lakes, MN (US); Brian T. Howard, Minneapolis, MN (US); Timothy G. Laske, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 812 days.

(21) Appl. No.: 18/190,695

(22) Filed: Mar. 27, 2023

(65) Prior Publication Data

US 2023/0310072 A1 Oct. 5, 2023

Related U.S. Application Data

(60) Provisional application No. 63/324,761, filed on Mar. 29, 2022.

(51) Int. Cl.

*A61B 18/12* (2006.01)
*A61B 18/14* (2006.01)
(Continued)

(52) U.S. Cl.

CPC *A61B 18/1492* (2013.01); *A61B 2017/00725* (2013.01); *A61B 2018/00357* (2013.01);
(Continued)

(58) Field of Classification Search

CPC ..... A61B 18/12; A61B 18/14; A61B 18/1492; A61B 18/1402; A61B 18/1206;
(Continued)

(56) References Cited

U.S. PATENT DOCUMENTS 10,245,429 B2 4/2019 Deem et al.
10,660,702 B2 5/2020 Viswanathan et al.
(Continued)

FOREIGN PATENT DOCUMENTS

WO 2021102230 A1 5/2021

OTHER PUBLICATIONS

International Search Report and Written Opinion for Application No. PCT/US2023/065044 dated Jul. 20, 2023 (17 pages).

*Primary Examiner* — Thomas A Giuliani
(74) *Attorney, Agent, or Firm* — Michael Best & Friedrich LLP

(57) ABSTRACT

A method and system for directed pulsed electric field (PEF) ablation are disclosed. In one aspect, an irreversible electroporation (IRE) system includes processing circuitry configured to select a first set of electrodes positioned to produce a first electric field in a first direction in a region of tissue of a patient, and select a second set of electrodes positioned to produce a second electric field in a second direction in the region of tissue. The processing circuitry is configured to transmit a first IRE pulse to the first set of electrodes to cause emission of the first electric field and transmit a second IRE pulse to the second set of electrodes to cause emission of the second electric field. The first IRE pulse and the second IRE pulse are transmitted by the processing circuitry to control an electric field gradient along a path within the region of tissue.

20 Claims, 8 Drawing Sheets

(51) Int. Cl.
*A61B 17/00* (2006.01)
*A61B 18/00* (2006.01)

(52) U.S. Cl.
CPC ............... *A61B 2018/00488* (2013.01); *A61B 2018/00613* (2013.01); *A61B 2018/0072* (2013.01); *A61B 2018/00755* (2013.01)

(58) Field of Classification Search
CPC .......... A61B 18/1233; A61B 2018/124; A61B 2018/1273; A61B 2018/00267; A61B 2018/00577; A61B 2018/00642; A61B 2018/00654; A61B 2018/0016; A61B 2018/0022; A61B 2018/00214; A61B 2018/0072; A61B 2018/00755; A61B 2018/00357; A61B 2018/00613; A61B 2018/00702; A61B 2018/00827; A61B 2018/00839; A61B 2018/167; A61B 2018/00666; A61B 2018/00636; A61B 2018/1467; A61B 2034/2053
USPC ............ 606/32, 34, 41, 42; 607/98, 99, 113, 607/115, 116
See application file for complete search history.

(56) References Cited

U.S. PATENT DOCUMENTS

| | | | | |
|---|---|---|---|---|
| 2007/0167942 | A1* | 7/2007 | Rick ...................... | A61B 18/16 606/35 |
| 2018/0071014 | A1* | 3/2018 | Neal ..................... | A61M 25/00 |
| 2019/0307500 | A1 | 10/2019 | Byrd et al. | |
| 2020/0275973 | A1 | 9/2020 | O'Brien et al. | |
| 2021/0169568 | A1* | 6/2021 | Govari ............... | A61B 18/1206 |
| 2021/0315639 | A1 | 10/2021 | Manucherhabadi et al. | |
| 2021/0369341 | A1 | 12/2021 | Gutbrod et al. | |
| 2022/0022952 | A1* | 1/2022 | Koop ................. | A61B 18/1492 |
| 2022/0047326 | A1 | 2/2022 | Altmann et al. | |

* cited by examiner

DIRECTED PULSED ELECTRIC FIELD ABLATION

CROSS-REFERENCE TO RELATED APPLICATION

This application claims priority to U.S. Provisional Application No. 63/324,761, filed on Mar. 29, 2022, the entire contents of which are hereby incorporated by reference.

FIELD

The present technology is generally related to directed pulsed electric field (PEF) ablation.

SUMMARY

Medical procedures are available for treating a variety of cardiovascular maladies, such as cardiac arrhythmias including atrial fibrillation, and other irregularities in the transmission of electrical impulses through the heart. As an alternative to open-heart surgery, many medical procedures are performed using minimally invasive surgical techniques, where one or more slender implements are inserted through one or more small incisions into a patient's body. Such procedures may involve the use of catheters or probes having multiple sensors, electrodes, or other measurement and treatment components to treat the diseased area of the heart, vasculature, or other tissue. Such procedures may involve the use of catheters or probes having multiple sensors, electrodes or other measurement and treatment components to treatment of other aspects of the patient condition such as renal denervation and cancer therapies, for example. Minimally-invasive devices are desirable for various medical and surgical applications because they allow for precise treatment of localized discrete tissues that are otherwise difficult to access. For example, catheters may be easily inserted and navigated through the blood vessels and arteries, allowing non-invasive percutaneous access to areas of the body selected for treatment.

One such example of a minimally invasive therapy involves the treatment of cardiac arrhythmias or irregular heartbeats in which physicians employ specialized cardiac assessment and treatment devices, such as mapping catheters and ablation catheters, to gain access to, diagnose, and treat interior regions of a patient's body. Such devices may include energized electrodes or other ablation assemblies to create lesions or other anatomical effects that disrupt or block cardiac conduction pathways through the targeted tissue.

In the treatment of cardiac arrhythmias, a specific area of cardiac tissue having aberrant electrically conductive pathways is typically initially identified for subsequent treatment. This localization or identification can include first using a non-invasive diagnostic method such as body surface mapping of the electrical activity of the heart or a minimally invasive diagnostic medical device such as a mapping catheter to obtain a baseline electrophysiological (EP) map of electrical activity in selected tissue. After mapping and diagnosing aberrant tissue, a physician may decide to treat the patient by ablating the tissue. An ablation procedure may involve creating one or more lesions to electrically isolate or kill tissue believed to be a source of an arrhythmia. One type of ablation is pulsed electric field (PEF) ablation, in which an electrical signal is applied to electrodes from within a catheter. An electrical signal may be sufficient to ablate the tissue that is in proximity to the electrodes.

Electroporation may be induced in tissues when an electric field of sufficient strength and duration is applied to cells in order to increase the permeability of the targeted cell membranes. Pulsed field ablation ("PFA") which can cause reversible or irreversible electroporation, is a primarily non-thermal ablation technique that creates lesions in desired areas of patient tissue by means of irreversible electroporation to treat conditions such as cardiac arrhythmias, and to ablate areas of tissues and/or organs in the body. For treating cardiac arrhythmias, for example, PFA can be performed to modify tissue by either killing the tissue directly or by reversibly increasing the cell permeability to temporarily disrupt the permeability of cell membranes in targeted tissue to allow the introduction of therapeutic agents into such cells which interrupt or prevent disease processes in order to stop aberrant electrical propagation and/or disrupt aberrant electrical conduction through cardiac tissue.

PFA includes application of short pulsed electric fields (PEF), which may reversibly or irreversibly destabilize cell membranes through electro-permeabilization, but generally do not affect the structural integrity of the tissue components, including the acellular cardiac extracellular matrix. The nature of PFA allows for very brief periods of therapeutic energy delivery, on the order of tens or hundreds of milliseconds in duration. Further, when targeting cardiomyocytes, PFA may not cause collateral damage to non-targeted tissue as frequently or as severely as thermal ablation techniques. Additionally, electrical conduction may be temporarily disrupted for diagnostic purposes or therapeutic agents may be preferentially introduced into the cells of targeted tissue that are exposed to a pulsed electric field (PEF) having reversible membrane permeabilization.

In some PFA systems, the user programs, or otherwise manually enters, the desired parameters of the pulsed electric field (PEF) to be delivered to the tissue. The PEF may be generated by an electrosurgical generator configured to deliver electrical energy to the target tissue through electrodes located on the end effector of an electrosurgical hand piece or electrodes located on an indwelling portion of one or more intracardiac catheters. Additional electrodes, generally of relatively larger surface areas may be located within other locations in the body or on the body surface to provide alternate current paths for therapeutic signals. For a given delivery tool, target tissue, or environment, the user may select from waveform parameters such as the amplitude, size, shape, frequency, and repetition of the waveform. These parameters affect a size of the lesion caused by application of the PEF.

The techniques of this disclosure generally relate to directed pulsed electric field (PEF) ablation. In one aspect, the present disclosure provides an irreversible electroporation (IRE) system. According to one aspect, the IRE system includes processing circuitry that may be configured to select a first set of electrodes positioned to produce a first electric field in a first direction in a region of tissue of a patient, and select a second set of electrodes positioned to produce a second electric field in a second direction in the region of tissue. The processing circuitry may also be configured to transmit a first IRE pulse to at least one electrode of the first set of electrodes to cause the at least one electrode of the first set of electrodes to produce the first electric field and transmit a second IRE pulse to at least one electrode of the second set of electrodes to cause the at least one electrode of the second set of electrodes to produce the second electric field. The first IRE pulse and the second IRE pulse may be transmitted by the processing circuitry to control an electric field gradient along a path within the region of tissue.

In addition to any combination of features described above, the first IRE pulse may be different than the second IRE pulse such that the first electric field has a different level of strength than the second electric field.

In addition to any combination of features described above, the processing circuitry may be configured to transmit a non-IRE test pulse to at least one of the group consisting of the first set of electrodes, the second set of electrodes, and a third set of electrodes to cause the at least one of the group consisting of the first set of electrodes, the second set of electrodes, and the third set of electrodes to generate a third electric field. The processing circuitry mal also be configured to receive, from at least one of the group consisting of the first set of electrodes, the second set of electrodes, the third set of electrodes, and a fourth set of electrodes, electrical signals indicative of the third electric field. The processing circuitry may also be configured to map electrical activity within the region of tissue based on the electrical signals indicative of the third electric field.

In addition to any combination of features described above, at least one electrode of the at least one of the group consisting of the first set of electrodes, the second set of electrodes, the third set of electrodes, and the fourth set of electrodes may be located external to the patient.

In addition to any combination of features described above, the processing circuitry may be configured to transmit the non-IRE test pulse, receive the electrical signals, and map the electrical activity at one or both of a time before and a time after an ablation procedure is performed on at least part of the region of tissue.

In addition to any combination of features described above, the IRS system may include a graphical user interface that includes a video display configured to receive and display a map of the electrical activity within the region of tissue onto a rendering of a patient anatomy that includes the region of tissue.

In addition to any combination of features described above, a first catheter may include the first set of electrodes and the second set of electrodes. Alternatively, a first catheter may include the first set of electrodes, and a second catheter may include the second set of electrodes.

In addition to any combination of features described above, the first catheter may be positioned in a first chamber of a heart of the patient, and the second catheter may be positioned in a second chamber of the heart of the patient.

In addition to any combination of features described above, the first catheter may be positioned in a chamber of a heart of the patient, and the second catheter may be positioned outside of the heart of the patient and in one of a pericardial space of the patient, an esophagus of the patient, and a substernal space of the patient.

In addition to any combination of features described above, the processing circuitry may be configured to control the first IRE pulse and the second IRE pulse to cause the electric field gradient to reach a target electric field gradient. The target electric field gradient may correspond to an electric field strength above a threshold throughout the region of tissue.

In addition to any combination of features described above, the first direction, the second direction, or both the first direction and the second direction may be selected to align with a polarization direction associated with polarizable cells of the region of tissue.

In addition to any combination of features described above, a first catheter may include the first set of electrodes, and the second set of electrodes may include an external electrode located outside of a body of the patient.

According to another aspect, an IRE system includes processing circuitry that may be configured to select a first set of electrodes positioned in a first area in proximity to a target region of tissue to be ablated, and select a second set of electrodes distributed over a second area. The processing circuitry may also be configured to determine a first IRE pulse to be applied to at least one electrode of the first set of electrodes to ablate the target region of tissue in proximity to the first set of electrodes at least partially using a first electric field emitted by the at least one electrode of the first set of electrodes. The processing circuitry may also be configured to determine a second IRE pulse to be applied to at least one electrode of the second set of electrodes to cause the at least one electrode of the second set of electrodes to emit a second electric field to interact with the first electric field in ablating the target region of tissue. The processing circuitry may also be configured to selectively apply the first IRE pulse to the at least one electrode of the first set of electrodes and the second IRE pulse to the at least one electrode of the second set of electrodes.

In addition to any combination of features described above, the processing circuitry may also be configured to adjust an impedance for each electrode of the at least one electrode of the first set of electrodes and each electrode of the at least one electrode of the second set of electrodes. The impedance may be adjusted by the processing circuitry based on a desired current for each electrode.

In addition to any combination of features described above, the desired current may be selected to be below an overcurrent condition threshold. The processing circuitry may also be configured to select the impedance for a first electrode to avoid an overcurrent condition for an IRE pulse determined to be provided to the first electrode.

In addition to any combination of features described above, the processing circuitry may also be configured to determine a target electric field gradient to provide an electric field strength above a threshold throughout a specified volume of the target region of tissue. The processing circuitry may also be configured to select the first set of electrodes and the second set of electrodes and selectively apply the first IRE pulse and the second IRE pulse to cause an electric field gradient throughout the specified volume of the target region of tissue to reach the target electric field gradient.

In addition to any combination of features described above, the at least one electrode of the second set of electrodes may be positioned with respect to a position of the at least one electrode of the first set of electrodes in order to produce a combined electric field in a direction aligned with a polarization direction associated with polarizable cells of the target region of tissue. The combined electric field may be produced by a combination of the first electric field and the second electric field.

In addition to any combination of features described above, the processing circuitry may also be configured to transmit a non-IRE test pulse to at least one of the group consisting of the first set of electrodes, the second set of electrodes, and a third set of electrodes. The processing circuitry may also be configured to receive electrical signals responsive to the non-IRE test pulse from at least one of the group consisting of the first set of electrodes, the second set of electrodes, the third set of electrodes, and a fourth set of electrodes. The processing circuitry may also be configured to map the electrical signals onto a rendering of a patient anatomy that includes the target region of tissue that is displayable on a video monitor.

In addition to any combination of features described above, the processing circuitry may also be configured to transmit the non-IRE test pulse, and receive and map the electrical signals, after the target region of tissue is at least partially ablated.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
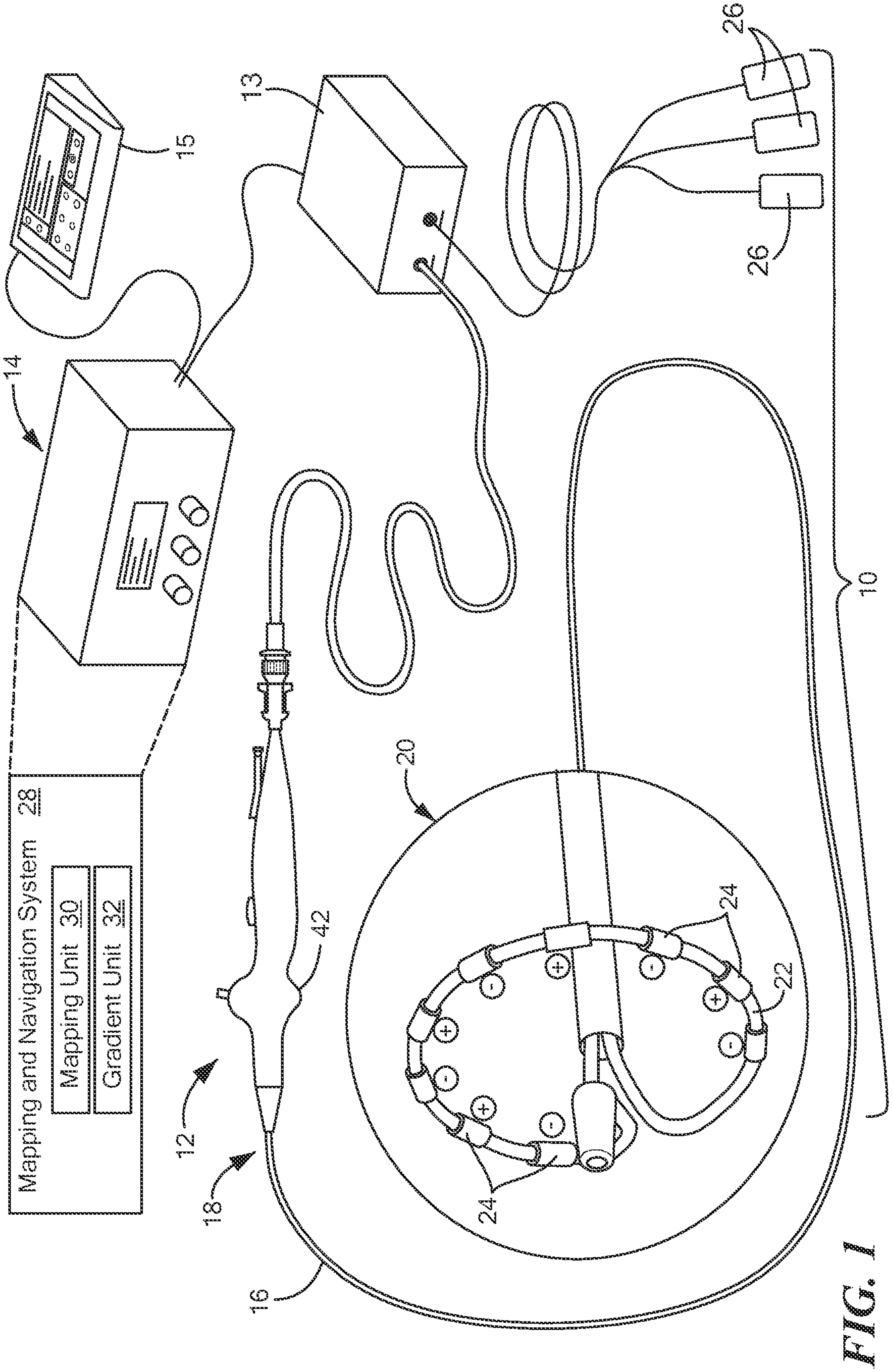
FIG. 1 is an illustration of one example pulsed field ablation system.

Before describing in detail exemplary embodiments, it is noted that the embodiments reside primarily in combinations of apparatus components and processing steps related to directed PEF ablation. Accordingly, components have been represented where appropriate by symbols in the drawings, showing only those specific details that are pertinent to understanding the embodiments so as not to obscure the disclosure with details that will be readily apparent to those of ordinary skill in the art having the benefit of the description herein. Like numbers refer to like elements throughout the description.

As used herein, relational terms, such as “first” and “second,” “top” and “bottom,” and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms “a”, “an” and “the” are intended to include the plural forms as well, unless the context clearly indicates otherwise. It will be further understood that the terms “comprises,” “comprising,” “includes” and/or “including” when used herein, specify the presence of stated features, integers, steps, operations, elements, and/or components, but do not preclude the presence or addition of one or more other features, integers, steps, operations, elements, components, and/or groups thereof.

In embodiments described herein, the joining term, “in communication with” and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

In some embodiments described herein, the term “coupled,” “connected,” and the like, may be used herein to indicate a connection, although not necessarily directly, and may include wired and/or wireless connections.

Referring now to the drawing figures, in which like elements are referred to by like reference numerals, there is shown in FIG. 1 an example of a PFA system configured to deliver electrical energy to reversibly or irreversibly electroporate tissue. The PFA system generally includes a medical device 12 that may be coupled directly to an energy supply, for example, a pulsed field ablation generator 14. The PFA generator 14 provides energy control, delivery, and monitoring directly or indirectly through a catheter electrode distribution system (CEDS) 13. An input device 15 may further be included in communication with the PFA generator 14 for operating and controlling the various functions of the PFA generator 14. The medical device 12 may generally include one or more diagnostic or treatment regions for energetic, therapeutic, and/or investigatory interaction between the medical device 12 and a treatment site. The PFA system may deliver, for example, pulsed electroporation energy to a tissue area in proximity to the treatment region (s). The PFA system may also include a display device to display information to the user.

The medical device 12 may include an elongate body 16 passable through a patient’s vasculature and/or position-able proximate to a tissue region for diagnosis or treatment, such as a catheter, sheath, or intravascular introducer. The elongate body 16 may define a proximal portion 18 and a distal portion 20, and may further include one or more lumens disposed within the elongate body 16 thereby providing mechanical, electrical, and/or fluid communication between the proximal portion 18 of the elongate body 16 and the distal portion 20 of the elongate body 16. The distal portion 20 may generally define the one or more treatment region(s) of the medical device 12 that are operable to monitor, diagnose, and/or treat a portion of a patient.

The treatment region(s) may have a variety of configurations to facilitate such operation. In the case of purely bipolar pulsed field delivery, distal portion 20 includes electrodes 24 that form the bipolar configuration for energy delivery where energy passes between one or more electrodes and one or more different electrodes on the same electrode array. In an alternate configuration, a plurality of the electrodes 24 may serve as one pole while a second device containing one or more electrodes (not pictured) would be placed to serve as the opposing pole of the bipolar configuration. For example, as shown in FIG. 1, the distal portion 20 may include an electrode carrier arm 22 that is transition-able between a linear configuration and an expanded configuration in which the carrier arm 22 has an arcuate or substantially circular configuration. The electrode carrier arm 22 may include the plurality of electrodes 24 (for example, nine electrodes 24, as shown in FIG. 1) that are configured to deliver pulsed-field energy. Further, the electrode carrier arm 22 when in the expanded configuration may lie in a plane that is substantially orthogonal to the longitudinal axis of the elongate body 16. The planar orientation of the expanded electrode carrier arm 22 may facilitate ease of placement of the plurality of electrodes 24 in contact with the target tissue. Alternatively, the medical device 12 may have a linear configuration with the plurality of electrodes 24. For example, the distal portion 20 may include nine electrodes 24 linearly disposed along a common longitudinal axis.

The PFA generator 14 may include processing circuitry including a processor in communication with one or more controllers and/or memories containing software modules containing instructions or algorithms to provide for the automated operation and performance of the features, sequences, calculations, or procedures described herein. For example, as shown in FIG. 1, the PFA generator 14 includes a mapping and navigation system 28, which may be implemented by processing circuitry 48 (e.g., including an electronic processor) within the PFA generator 14. The mapping and navigation system 28 includes a mapping unit 30 and a gradient unit 32 that may be implemented by the processing circuitry 48 as explained in greater detail below (e.g., with respect to FIG. 3). The mapping and navigation system 28 performs a mapping of electrical signals onto a two or three dimensional rendering of the heart (or other organ(s)). Such mapping can be displayed in a two-dimensional or three-dimensional rendering. The mapping unit 30 performs a mapping of electrical signals, catheter positions and electrode positions onto a two or three dimensional rendering of the heart or a portion or chamber thereof. The gradient unit 32 may be configured to determine an electric field gradient between any two points along lines or contours. An electric field gradient indicates a change in electric field as a function of position. For example, an electric field might change as a linear function of position. Advantages of the mapping and gradient determination include a more accurate control over the electric field applied to the tissue, and consequently, a more accurate result of the ablation procedure.

As used herein, the terms "map" or "mapping" are used to describe the collection of cardiac biophysical electrical data by means of body surface electrodes 58 or indwelling electrodes 56 that measure electrical activity occurring during the cardiac cycle of the heart. Measurements made during mapping may include voltages measured throughout the timing of cardiac cycles. In the case of body surface electrodes 58, such cardiac electrical activity may be determined as a result of calculations based on a plurality of non-contact measurements of such cardiac electrical signals at specific remote locations of a plurality of body surface electrodes 58. Assignment of such voltages to the cardiac surfaces (or representative geometry) may be made in conjunction with renderings of the cardiac structures based most commonly on cardiac tomography (CT) or magnetic resonance imaging (MRI). Voltage measurements made from intracardiac catheter electrodes 56 may be associated with specific locations on or within the cardiac tissues. Such rendered images of the cardiac structures which include the time-based electrical data may be considered to be "electro-anatomical maps".

The mapping of electric field gradients may be accomplished using any combination of catheters and/or electrodes associated with the patient. For example, some catheters and/or electrodes may be dedicated "monitoring" catheters or electrodes that are configured to be used to gather electric signals (from other catheters and/or electrodes) that are used by the processing circuitry 48 to map electric field gradients. As another example, some catheters and/or electrodes may be dedicated PEF energy delivery devices for ablation and/or testing purposes. As yet another example, catheters and/or electrodes may be used for PEF energy delivery at some times but also used as "monitoring" catheters or electrodes at other times. In some instances, some electrodes on a first catheter may have different functions than other electrodes on the first catheter at all times or at some times.

The PFA system 10 may further include three or more surface ECG electrodes 26 on the patient in communication with the PFA generator 14 through the catheter electrode distribution system (CEDS) 13 to monitor the patient's cardiac activity for use in determining pulse train delivery timing at the desired portion of the cardiac cycle, for example, during the ventricular refractory period. In addition to monitoring, recording, or otherwise conveying measurements or conditions within the medical device 12 or the ambient environment at the distal portion 20 of the medical device 12, additional measurements may be made through connections to the multi-electrode catheter including for example temperature, electrode-tissue interface impedance, delivered charge, current, power, voltage, work, or the like in the PFA generator 14 and/or the medical device 12.

The surface ECG electrodes 26 may be in communication with the PFA generator 14 for initiating or triggering one or more alerts or therapeutic deliveries during operation of the medical device 12. Additional neutral electrode patient ground patches (not pictured) may be employed to evaluate the relative unipolar and bipolar electrical path impedance, as well as monitor and alert the operator upon detection of inappropriate and/or unsafe conditions, which include, for example, improper (either excessive or inadequate) delivery of charge, current, power, voltage and work performed by the plurality of electrodes 24; improper and/or excessive temperatures of the plurality of electrodes 24, improper electrode-tissue interface impedances; improper and/or inadvertent electrical connection, or inadequate dielectric protection between circuit. This aids in evaluation of the patient prior to delivery of high voltage energy by delivering one or more low voltage test pulses (e.g., non-IRE test pulses) to evaluate the integrity of the tissue electrical path.

The terms "bipolar" and "unipolar" may in some cases be relative (for example, in radio frequency (RF) ablation). An electrical conduction between an ablation electrode or set of electrodes of relatively small surface area and an electrode having a large surface area (such as a skin patch patient return electrode (PRE)), may be referred to as unipolar conduction. In contrast, an electrical conduction between electrodes of similar surface area on the same catheter may be referred to as bipolar conduction. Electrical conduction between electrodes of different catheters may be considered bipolar or unipolar, depending on relative electrode surface areas. For example, when electrodes of different catheters have similar surface areas, each catheter may be operated as a unipolar device with a bipolar current flowing between them.

The PFA generator 14 may include an electrical current or pulse generator 50 (see FIG. 3) having a plurality of output channels, with each channel coupled to an individual electrode of the plurality of electrodes 24 or multiple electrodes of the plurality of electrodes 24 of the medical device 12. The PFA generator 14 may be operable in one or more modes of operation, including for example: (i) bipolar energy delivery between at least two electrodes 24 or electrically-conductive portions of the medical device 12 within a patient's body, (ii) monopolar or unipolar energy delivery to one or more of the electrodes or electrically-conductive portions on the medical device 12 within a patient's body and through either a second device within the body (not shown) or a patient return or ground electrode (not shown) spaced apart from the plurality of electrodes 24 of the medical device 12, such as on a patient's skin or on an auxiliary device positioned within the patient away from the medical device 12, for example, and (iii) a combination of the monopolar and bipolar modes.

Figure 2:
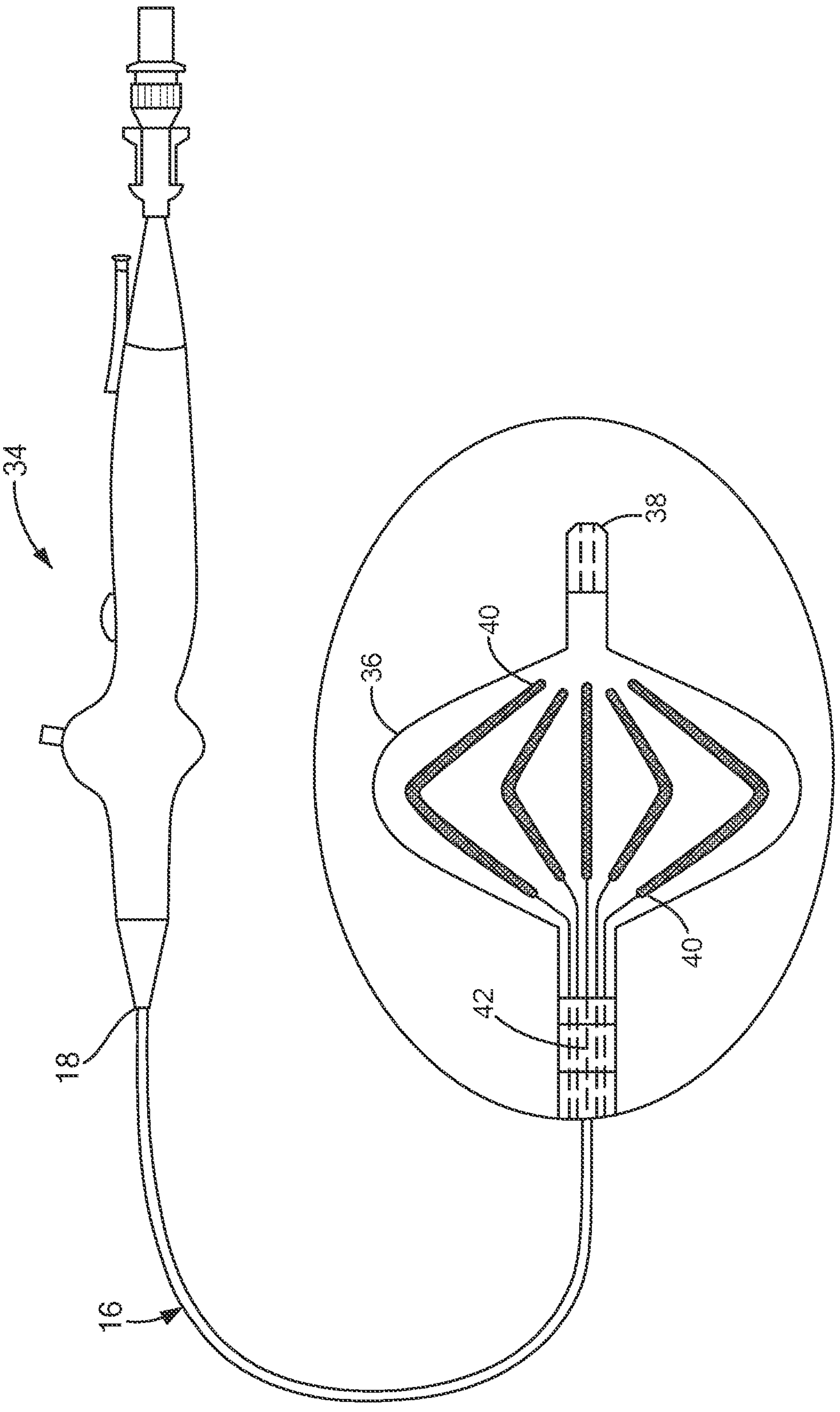
FIG. 2 is an illustration of one example of a catheter device, showing a plurality of electrodes or electrode arrays.
Figure 3:
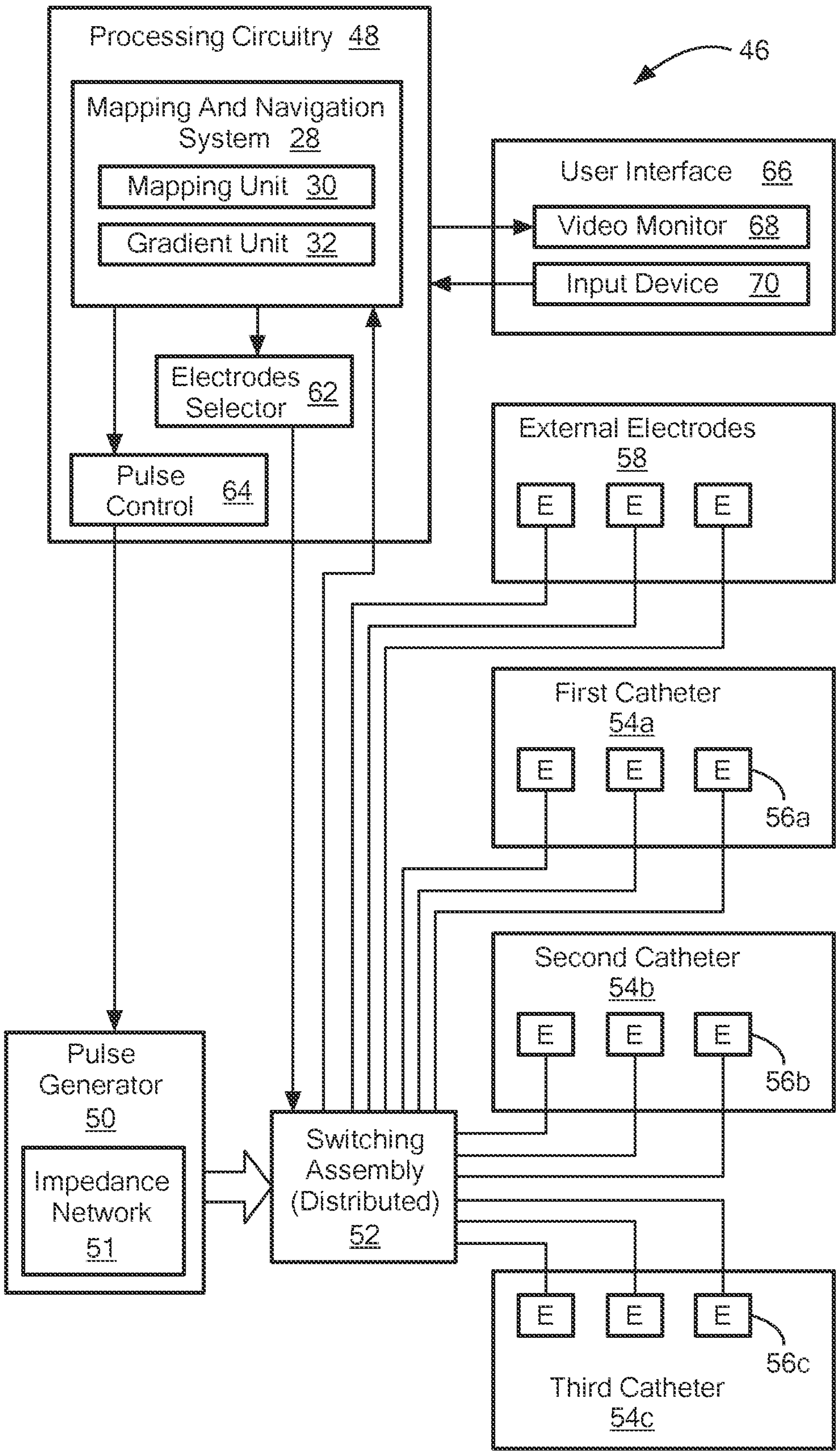
FIG. 3 is a block diagram of an example of an IRE system constructed according to principles disclosed herein.

FIG. 2 shows an alternative type of catheter device 34 that has a ballooning or expanding section 36 at or near a distal end 38 of the catheter device 34. Other types of catheters may be used in some embodiments, including other types of expandable catheters. For example, an electrode array may be supported by an expandable elastic device or mesh structure. In the example of FIG. 2, the balloon device may also be designed without a tip, such that it would be more suitable for placement of the distal end 38 and placing electrodes against cardiac walls, for example. The balloon device may also be designed to incorporate an internal lumen (not shown), through which a guide wire may be passed. The ballooning section 36 has electrodes 40. Electrodes 40 may be one or more electrodes such as an array of electrodes. For example, one electrode may consist of a plurality of smaller electrodes connected by one or more electrical conductors in some embodiments. Wires 42 may couple electrical signals to the electrodes 40. When the ballooning section 36 is caused to inflate or expand, the electrodes 40 may be pressed against surrounding tissue and sense electrical activity in the tissue in the vicinity of the electrodes 40. The electrical activity sensed by the electrodes 40 may be conducted by the wires 42 to equipment that is switchably connected to the electrodes 40 and that records and displays the electrical activity sensed by the electrodes. Such equipment may include an electrocardiograph (ECG), electrophysiological mapping and recording system, a computer with a keyboard, mouse and video monitor (e.g., user interface 66 including video monitor 68 and input device 70 as shown in FIG. 3). The signals that are displayed on the video monitor may assist the surgeon in determining, among other things, an amount of electrical activity of the tissue and how well the expandable member is making contact with the surrounding tissue and whether the ablation in a current position is likely to succeed or whether the ballooning section 36 should be repositioned and a new mapping obtained. An irreversible electroporation (IRE) pulse may be applied to one or more of the electrodes 40 to ablate the tissue of a targeted region of tissue. Alternatively, a reversible electroporation pulse may be applied to determine an impact on local electrical activity. The electrodes 40 may be connected by the wires 42 to a switching assembly 52 shown in FIG. 3, which may be located within the PFA generator 14. The ballooning section 36 may have a plurality of electrodes 40 which are positioned along multiple lines. The electrodes 40 along any line may be activated individually, in pairs of electrodes 40 or in sets of more than two electrodes 40. Also, electrodes 40 belonging to different lines can also be selectively activate individually, in pairs or in sets of more than two. Thus, for example an electrode 40 along one line may be paired with an electrode 40 along another line or the same line, and an electric field gradient can be created between them by applying a voltage to the electrodes 40 in the pair.

FIG. 3 is a block diagram of an example embodiment of an irreversible electroporation (IRE) system 46 configured to selectively apply signals to certain electrodes to achieve a desired electric field gradient within a region of the body of a patient, for example, the patient's heart.

In the example of FIG. 3, the IRE system 46 includes processing circuitry 48, a pulse generator 50 and one or more switching assemblies 52. In some embodiments, the switching assemblies 52 are located at a distance from the catheter, such as in the PFA generator 14. Some or all of the one or more switching assemblies 52 may be located at a distal end of one or more catheters. Each one of one or more catheters 54, for example catheters 54*a*, 54*b* and 54*c*, has electrodes 56 (labelled E in FIG. 3) located at a distal end of a respective catheter 54. The processing circuitry 48 may be configured to control pulses of a pulse generator 50 capable of generating non-ablating (reversible) test pulses (e.g., non-IRE test pulses) and generating irreversible electroporation (IRE) pulses. Such reversible pulses and irreversible pulses may differ in amplitude, frequency and duration. For example, pulses may include diagnostic pulses that stimulate excitable cells (to evaluate a normal contractile function of cardiac muscle tissue, for example, or to measure an electrical characteristic such as impedance, for example. Such diagnostic pulses have no electroporation effect (reversible or irreversible). The pulses may include irreversible electroporation (IRE) ablation pulses which are intended to ablate tissue. The pulses may include pulses having a transient effect upon tissue by temporarily increasing cell permeability. These pulses may have lower voltage and longer duration, for example, than IRE pulses. Application of reversible pulses may be part of a therapy to introduce genetic material or large molecules into targeted tissue to treat certain diseases. Cells to which such reversible pulses are applied generally will survive and recover from transient hyper-permeability to regain cell functionality.

The pulse generator 50 may include a configurable impedance network 51 that can be configured to provide an impedance in any path toward an electrode 56. Note that in some embodiments, the electric field vectoring may be applied to produce a certain electric field distribution between electrodes 56 on the same catheter 54. In some embodiments, non-IRE (reversible) pulses may be delivered via therapeutic pathway for mapping in order to determine the impact that the irreversible pulse will have on an arrhythmia. In some embodiments, an impedance for an electrode 56 is selected based on a measured impedance or correlation value for one or more other electrode(s) 56. An impedance for each electrode 56 may be individually selected to receive an IRE pulse of the set of IRE pulses, the impedance being adjusted based on a desired current for the electrode 56. In some instances, a first IRE pulse transmitted (e.g., by the pulse generator 50 based on instructions from the processing circuitry 48) to a first set of electrodes 56*a* configured to generate a first electric field is different than a second IRE pulse transmitted to a second set of electrodes 56*b* configured to generate a second electric field. For example, different impedances may be provided on different paths toward different electrodes 56 in order to provide the difference (e.g., a difference in level of strength of the electric fields) between the first IRE pulse and the second IRE pulse. Other characteristics of the IRE pulses (e.g., duration, frequency, etc.) may be controlled by the processing circuitry 48 and/or the pulse generator 50 to provide differences between IRE pulses that are provided to different electrodes 56 (and/or 58). In instances where the first IRE pulse is different than the second IRE pulse, the first electric field may have a different level of strength (e.g., varying level of energy) than the second electric field that is, for example, caused by differences in impedance provided by the impedance network 51 for each signal that is transmitted to the electrodes 56. While a first IRE pulse and a second IRE pulse are explained in the above example, additional IRE pulses may be transmitted to the same or different electrodes 56 as the electrodes 56 that respectively receive the first IRE pulse and the second IRE pulse. Additionally, in some instances, different sets of electrodes 56 may receive the same IRE pulse.

The system 46 may be directed to measure impedances at different frequencies in various vectoring arrangements between electrodes 40, to determine the optimal vectors through which to deliver high voltage pulses to ablate a targeted region of tissue. Impedance may be measured from electrode(s) 40 to the body surface or may be measured between electrodes. High frequency measurements detect the capacitive nature of tissue in contact with the electrodes 40 while lower frequency measurements detect the more purely resistive impedance of tissues. Measurements at lower frequencies of 10-25 kHz may be compared to impedances measured at frequencies of 100-500 kHz to determine quality of tissue contact versus blood contact (i.e., how much of an electrode surface is in contact with muscle tissue as opposed to blood, for example. Comparison of impedances measured at low and high frequencies may also be used to determine surrounding tissue characteristics between two or more measuring electrodes 40, relating to what could be expected when high voltages are applied to these electrodes.

The electrodes 56 can be selectively connected or disconnected from the pulse generator 50 by switches of the switching assembly 52 which may be within the respective catheter 54 having the electrodes 56 or in an external control system embedded within other system hardware. Although three catheters 54*a*, 54*b* and 54*c* are shown in the example of FIG. 3, fewer or greater than three catheters 54 may be positioned within the patient. Also, although the example of FIG. 3 shows three electrodes 56 within each catheter 54, fewer or greater than three electrodes 56 may be included within any given catheter(s) 54. In some embodiments, some or all of the electrodes 56 of a catheter 54 may be configured to be in electrical series and/or to be electrically parallel.

In the example of FIG. 3, the IRE system 46 includes external electrodes 58 which may be positioned externally on the body of the patient or in other locations within the body of the patient. The external electrodes 58 may be selectively connected or disconnected by one or more switches of the switching assembly 52. As noted, some or all of the switching assemblies 52 may be distributed within the body and/or be external to the body. For example, the switching assembly 52 may include switches that are distributed within a body of the catheter 54 or positioned closer to the electrodes selector 62. The one or more switches of the switching assembly 52 may be controlled by the electrodes selector 62, which in turn is controlled by the mapping and navigation system 28. The various combinations of electrodes 40 that may be activated individually or in groups may be selected by the electrodes selector 62. The switches of the switching assembly 52 may be implemented by vacuum protected mechanical relays which are located within the CEDS unit or an energy direction and vectoring control unit implemented by the processing circuitry 48. In some embodiments the switches of the switching assembly 52 may be implemented as micro-electromechanical systems (MEMS) which are small enough to be incorporated into the structure of the catheter 54 or within the handle of the catheter 54.

Also note that some electrodes 56 may have been implanted in the body during a prior surgery, for example, as a part of an implantable pacing or defibrillation system. Some of the switches of a switching assembly 52 may be located within a catheter 54, or external to the catheter 54. In some embodiments, the electrodes 56 may be placed in a first position for non-ablative testing and may be placed in a second position for IRE pulse delivery. Alternatively, a first set of electrodes 56*a* may be used for non-ablative testing and a second set of electrodes 56*b* may be used for ablation. Some electrodes 56 in the first set may be the same electrodes 56 as some of the electrodes 56 in the second set. In general, non-ablative testing (e.g., using non-IRE test pulses) may include the application of substantially lower amplitudes or energies than for ablation and substantially longer pulse widths and fewer pulses than for corresponding ablative pulse parameters. For example, non-ablative testing may include applying diagnostic currents to measure electrical properties of tissue, such as impedance. Non-ablative testing may include applying stimulation pulses such as pacing pulses to measure healthy contractile tissue function. Non-ablative testing may include applying currents for cardiac navigation, for example. Non-ablative testing to determine impedance or for navigation may include high frequency (e.g., >10 kHz) pulse trains, whereas non-ablative testing to stimulate or pace excitable muscle tissue may include direct current pulses in the 0.5 ms to 2 ms range. In some instances, the processing circuitry 48 controls the pulse generator 50 to provide a signal to one or more electrodes 56 to generate test pulses to ensure that a minimum impedance exists between each set of electrode pairs that are planned to receive IRE pulses to perform ablation. In some instances, ensuring that such electrode pairs have the minimum impedance between them may avoid electrical shorts and/or may manage current density to avoid coagulum/char formation. When the minimum impedance does not exist between an electrode pair, the processing circuitry 48 may prevent the IRE pulses from being provided to the electrode pair, for example, until the electrode pair is adjusted to result in the minimum impedance being present between the two electrodes 56. The term "stunning" refers to transiently stunning cells to cause those cells to lose contractile function for several minutes, for example, to diagnose an arrhythmogenic condition in the patient's heart.

Vectoring may be different for the first and second set of electrodes 56 which distributes the electric field in a way that avoids high field gradients and produces a more uniformly distributed field strength which produces reversible effects. Specific electrode vectoring schemes that are measured to have low resistance may be expected to result in high currents which may result in excessive electric field gradients near certain electrodes 56. Having two sets of electrodes positioned at an appropriate distance to promote such a distribution will be effective in reversibly affecting selected tissues to temporarily render them inactive, e.g., to test if these tissues should be targeted for irreversible electroporation.

The processing circuitry 48 has the mapping and navigation system 28, an electrodes selector 62, and a pulse controller 64. The processing circuitry 48 interacts with a graphical user interface 66 that enables an operator of the IRE system 46 to input data and controls and to visualize outputs of the mapping and navigation system 28. The mapping and navigation system 28 performs a mapping of electrical signals (e.g., indicative of an electric field gradient) onto a two or three dimensional rendering of a patient anatomy including a targeted region of tissue (e.g., a rendering of the heart, other organ(s), etc.) and causes display of such mapping and rendering on a video monitor 68 of the user Interface 66. For example, heart tissue may be represented in an anatomical rendering of the heart chamber and the electrodes 56 of the ablation and diagnostic devices may be rendered on the video monitor 68. The user may select the area they intend to target for ablation but the system 46 may determine which set or sets of electrodes 56 should be energized to most effectively ablate the tissue target indicated by the user. For example, the processing circuitry 48 may include a memory that stores a look-up table of desired polarization directions and/or desired electric field strengths for a plurality of regions of a patient anatomy. Based on the user input of a selected area of the patient anatomy and optionally based on other received user inputs (e.g., a maximum energy level to be used by a certain set of electrodes 56), the processing circuitry 48 may select one or more sets of electrodes 56 and determine one or more pulses (e.g., IRE pulses) to be applied to the selected sets of electrodes 56. An input device 70, such as a keyboard and mouse or input device 15, or a touchscreen or tactile remote control allowing specific electrode selections and energy delivery levels, enables the operator to control operation, functionality, and state of the IRE system 46 and to interact with a display on the video monitor 68. Some of the components of the IRE system 46 may be within the PFA generator 14, while some other components, such as the catheters 54 and the switching assembly 52 may be located in catheter devices 34.

The processing circuitry 48 may be implemented at least in part by an electronic processor (e.g., a computer processor or microcontroller) operating under the directions of software stored in a memory, and/or may be implemented as applications specific integrated circuitry (ASIC). Such software directions may be programmed by a computer programmer to cause the computer to perform the functions disclosed herein. Although this disclosure primarily focuses on applications of the IRE system 46 to the human heart, the methods and systems disclosed herein may be applied to other organs or other tissue. Note that the mapping may include mapping and display of the impact of the pulses on the electrical activity of the heart and may also include displaying an overlay of the gradients that will be produced by a particular electrode configuration on the mapping and navigation systems.

The mapping and navigation system 28 includes a mapping unit 30 and a gradient unit 32. The mapping unit 30 performs a mapping of electrical signals, catheter positions, electrode positions onto a two or three dimensional rendering of the heart or a portion or chamber thereof. The gradient unit 32 may be configured to determine an electric field gradient between any two points, lines or contours. An electric field gradient indicates a change in electric field as a function of position. For example, an electric field might change as a linear function of position. The electrical gradients measured via subtherapeutic pulses between various electrodes 56 may be supplemented through numerical modeling performed by the processing circuitry 48, for example through the use of Maxwell's equations to translate measured currents into electrical fields.

The electric field gradient determined by the gradient unit 32 may be displayed by the video monitor 68 either alone or overlaying the two or three dimensional rendering of the heart (or other patient anatomy including a target region of tissue). In some embodiments, the positions of the catheter(s) 54 and the electrodes 56 may be displayed by the video monitor 68 overlaying the two or three dimensional rendering of the heart via the video monitor 68. As the operator of the IRE system 46 moves a catheter 54, the movement may be displayed on the video monitor 68 (e.g., based on tracking methods involving the use of signals from the electrodes 56 themselves and/or based on tracking methods that use an external instrument tracking system). This display of the positions of the catheters 54 and/or electrodes 56 may be as an overlay of the rendering of the heart, or may be displayed in some other manner at the selection of the operator. For example, the catheters 54 and/or electrodes 56 may be displayed in a first color, a cavity of a heart or blood vessel may be displayed in a second color and walls of the heart or blood vessels may be displayed in a third color. In addition, mapping unit 30 may map a gradient of colors to different parts of the heart and blood vessels. A catheter 54 may be similar to the catheter shown in FIG. 1 or FIG. 2, except that in the catheter 54, there may be switches of one or more switching assemblies 52 configured to select one or more electrodes 56 to receive one or more non-ablative pulses and/or one or more IRE pulses.

The electrode(s) selector 62 is responsive to input by an operator of the IRE system 46 via the input device 70 (which may be a keyboard and mouse). The inputs by the operator may include a selection of one or more electrodes 56 and/or 58 to which non-ablative test pulses (e.g., non-IRE test pulses) or IRE pulses are to be applied. The inputs by the operator may include a shape, duration, repetition rate and amplitude of the pulses to be generated by the pulse generator 50. The pulse parameters input by the operator may be translated by the pulse controller 64 to control signals delivered to the pulse generator 50. These control signals are configured to cause the pulse generator 50 to generate pulses according to the input pulse parameters. The inputs by the operator may also include a designation of an area of the heart to be ablated, which may be done at least in part, graphically. The operator may also be able to select between reversible and irreversible energy levels.

The inputs by the operator enable selection by the processing circuitry 48 of electrodes 56 between which an electric field grating is to be determined and displayed. For example, the processing circuitry 48 may select a first set of electrodes **56*a* to which first electrical signals are applied and select a second set of electrodes 56*b* to which second electrical signals are applied. The first set of electrodes 56*a* may include at least one excitation electrode 56 to which first electrical signals are applied and at least one counter-electrode 56, 58 which may be grounded. The at least one excitation electrode 56 may be oriented with respect to the at least one counter-electrode 56, 58 in such a way that the first electrical signals applied to the excitation electrode(s) 56 produce a desired electric field gradient between the excitation electrode(s) 56 and the counter-electrode(s) 56, 58, as determined by the gradient unit 32**.

More particularly, the electrodes **56*a* in the first set may be excited by the first electrical signals to produce a first desired electric field gradient in a first orientation passing through a region of tissue to be tested or ablated. Similarly, the electrodes 56*b* in the second set may be excited by the second electrical signals to produce a second desired electric field gradient in a second orientation passing through the region of tissue to be tested or ablated. The first and second orientations may be orthogonal or at an acute angle. For a given set of electrode positions and for a given pulsed field waveform, the cells are more easily electroporated (lower IRE threshold) if they are parallel to the electric field direction. Therefore, it may be preferred to orient the electrodes 56 to produce an electric field in the direction of easier electroporation for specific tissue. Alternatively, the electrodes 56 may be oriented to deliver energy through multiple vectors to electroporate in different directions. By orienting the electrodes 56 (by positioning the catheters 54, for example) to be orthogonal, or at an operator-specified acute angle, a more controlled and/or uniform ablation may be achieved within the region of tissue desired to be ablated. Also, the first orientation may be chosen to be a first direction in which tissue cells within a first region of tissue are not easily electroporated and the second orientation may be chosen to be a second direction in which the tissue cells within a second region of tissue are easily electroporated. In some embodiments, when the orientation of the electric field is parallel to a long axis of the cells or, in some cases, the short axis of cells with high aspect ratio, such as myocytes and muscle cells, the cells are affected more than when an orthogonal orientation is applied. When such a configuration is used, one possible set of orthogonal directions would be an electrode 56 on one catheter 54 to a laterally placed electrode on another as one vector, and a pair of electrodes 56 on the first catheter 54***a* defining an approximately orthogonal vector to the electrodes 56 on a second catheter 54*b*. In some cases, vectors may be oriented to achieve the greatest electroporation in one area of tissue, while minimizing electroporation of other areas of tissue.

As explained previously herein, the processing circuitry 48 may include a memory that stores a look-up table of desired polarization directions, desired electric field strengths, and/or other ablation properties for a plurality of regions of a patient anatomy. Based on the user input of a selected area of the patient anatomy and optionally based on other received user inputs (e.g., a maximum energy level to be used by a certain set of electrodes 56 at a certain location, user-selected angle of electric field, shape, duration, repetition rate and amplitude of the pulses, etc.), the processing circuitry 48 may select one or more sets of electrodes 56 and determine one or more pulses (e.g., IRE pulses) to be applied to the selected sets of electrodes 56.

In some embodiments, the electrodes 56 are slidable on a catheter 54 such that they could be selectively slid closer together or farther apart. For example, the electrodes 56 on the outer surface of a delivery sheath which is delivering a device with a second set of electrodes 56 may be selected to be separated by the operator while watching the predicted effects of a delivery on the rendered image of the organ being treated.

In some embodiments, a user-selected electric field gradient between electrodes 56 or sets of electrodes 56 can be constant or linear with respect to distance between the electrodes 56 according to the voltage applied to the electrodes 56. The electric field gradient between electrodes 56 may be determined based at least in part on knowledge of the distance between the electrodes 56, the inherent physical properties of the heart (or other target tissue/anatomy) and surrounding tissues and an amplitude of the voltage applied across the electrodes.

In some embodiments, the processing circuitry 48 of the IRE system 46 may select a first set of electrodes 56*a* that are in close proximity to a region of tissue to be tested or ablated and a second set of electrodes 56*b* that are more distant from the region of tissue than the first set of electrodes 56*a*. In some embodiments, the first set of electrodes 56*a* are densely concentrated around at least a part of a boundary surrounding the region of tissue to be tested or ablated, and the second set of electrodes 56*b* are more distantly positioned from the region of tissue and are configured to provide a larger total electrode surface area of the second set of electrodes 56*b*. With such a configuration, a concentrated field may be applied to just the region of the tissue at a first electric field strength that decays to a lower value outside the region of tissue. In some instances, the processing circuitry 48 may be configured to select the two sets of electrodes 56*a* and 56*b* to cause the electric field gradient along a path within a target region of tissue to be ablated to reach a target electric field gradient. The target electric field gradient may correspond to an electric field strength above a threshold throughout the region of tissue (e.g., a threshold electric field strength to cause IRE at the target region of tissue, which may be pre-programmed/stored in a memory of the processing circuitry 48). In some instances, the processing circuitry 48 may additionally or alternatively be configured to control the first IRE pulse and the second IRE pulse that are respectively provided to the electrodes 56*a* and 56*b* to cause the electric field gradient to reach the target electric field gradient. In some instances, the processing circuitry 48 may receive one or inputs (via the input device 70) that establish user-desired values of, for example, a target location of the patient anatomy to be ablated, a maximum electric field for a given electrode 56 at a given non-target location, and/or the like. Based on the one or more inputs, known/stored values such as the threshold electric field strength to cause IRE, and determined locations of one or more catheters 54/electrodes 56, 58, the processing circuitry 48 may select one or more sets of electrodes and determine an IRE pulse to be transmitted to each of multiple electrodes 56 to perform ablation at the target location while remaining within the user-desired values with respect to non-target locations. In some instances, the processing circuitry 48 may determine multiple possible delivery paths that meet the user-desired values (e.g., through the use of different combination of electrodes 56, 58). In some instances, the processing circuitry 48 may control the video monitor 68 of the user interface 66 to display the multiple possible delivery paths (e.g., allow the user to scroll through displaying of multiple possible electric field gradients overlaid on a rendering of the patient anatomy) in order to allow the user to select a desired delivery path/electric field gradient.

In some embodiments, the processing circuitry 48 may display to the operator via the video monitor 68, the position of each electrode 56 within the body of the patient. The video monitor 68 may be caused to display and may highlight each electrode 56 selected by the operator and to further display an electric field map of the electric field resulting from an actual application of electrical signals to one or more of the selected electrodes 56. In some embodiments, the mapping and navigation system 28 may display an electric field map of an electric field that is determined to be a result of an application of signals to the selected electrodes 56, the applied signals being proposed by the operator. The electric field maps may be displayed overlaying a two or three dimensional rendering of the heart and body, for example.

Figure 4:
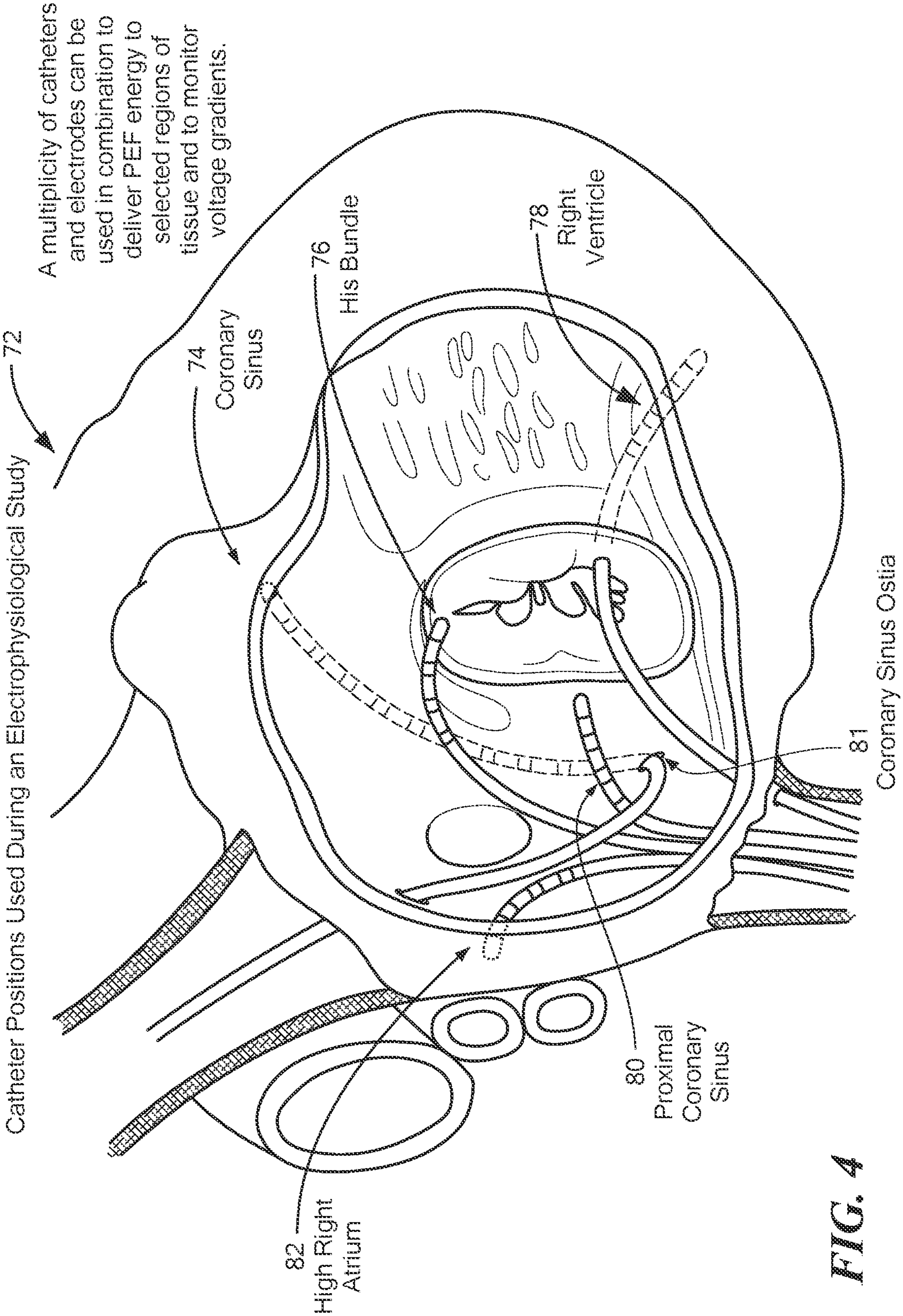
FIG. 4 illustrates a heart with catheters.

FIG. 4 illustrates a human heart 72 with a plurality of catheters 54 in positions that may be used in the electrophysiological mapping and ablation procedure including positions in vicinity of the coronary sinus 74, His bundle 76, right ventricle 78, proximal coronary sinus 80, coronary sinus ostia 81, and high right atrium 82. The plurality of catheters 54 positioned as shown can be used to deliver pulsed field energy and to monitor voltage gradients. For example, test pulses (e.g., non-IRE test pulses) can be delivered between a catheter 54 in/near the right ventricle 78 and a catheter 54 in/near the His bundle 76, with the electric field measured on catheters 54 in/near the coronary sinus 74, the proximal coronary sinus 80, and/or the high right atrium 82 to aid in the creation of a map of the resultant voltage gradients within the heart. Although not shown in FIG. 4, one or more catheters 54 may be additionally or alternatively located within one or both of the pulmonary arteries (e.g., entering the tricuspid valve, then passing into the right ventricle outflow tract, and then into one of the pulmonary arteries).

Figure 5:
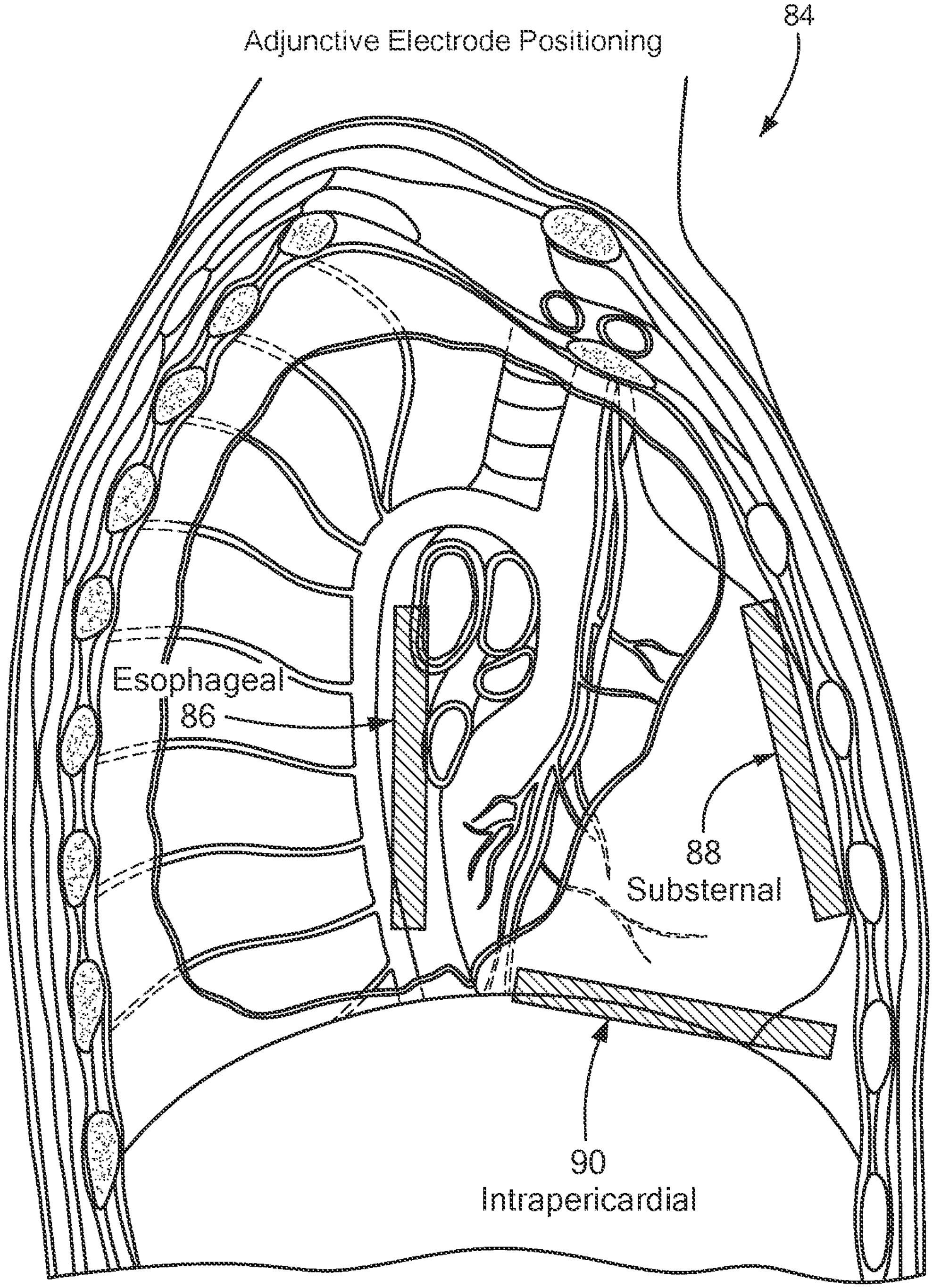
FIG. 5 illustrates an upper body with catheters external to the heart.

FIG. 5 illustrates a cross-sectional view of an upper portion 84 of a patient's body with the patient facing toward the right and including esophageal electrode array 86 (e.g., electrodes 56 of a catheter 54 positioned in the esophagus of the patient), substernal electrode array 88 (e.g., electrodes 56 of a catheter 54 positioned in the substernal space of the patient), and intrapericardial electrode array 90 (e.g., electrodes 56 of a catheter 54 positioned in the pericardial space of the patient). The electrodes 56 positioned in the pericardial space may be positioned in the pericardial space that is outside of the heart but that is within the coronary sinus 74 or cardiac veins (e.g., a pulmonary artery or other selected great vessel). The placement of one or more of these electrode arrays 86, 88, 90 in the areas shown in FIG. 5 that are outside of a heart of the patient may increase an ability to accurately sense electrical activity in a targeted region of tissue and/or to increase an ability to accurately ablate a targeted region of tissue (e.g., within the heart) while not ablating surrounding tissue. The positions of the catheters 54 shown in FIGS. 4 and 5 are examples only. These examples provide additional catheter locations for directing/steering fields towards targeted tissues which may be at the perimeter of the heart or may be adjacent to thicker tissues or tissues requiring high ablation energies/gradients. For example, one or more of the electrode arrays 86, 88, 90 may be part of a second catheter 54*b* that is located outside of a heart of the patient. The second catheter 54*b* may be used in conjunction with a first catheter 54*a* that is located within the heart of the patient. For example, both the first catheter 54*a* and the second catheter 54*b* may include electrodes 56 that are controlled by the processing circuitry 48 to receive pulses for testing and/or ablation as explained herein.

While the second catheter 54*b* is described as being outside of the heart in the above examples with respect to FIG. 5, the second catheter 54*b* may be located inside the heart in other instances (i.e., both catheters 54 located within the heart), for example, as indicated in FIG. 4. In some instances, the two catheters 54 may be placed in different locations and/or the processing circuitry 48 may control different electrodes 56 to provide electric fields corresponding to a desired electric field gradient along a path within a region of tissue to be ablated (e.g., based on user inputs as described previously herein). Additionally, while two catheters 54 (e.g., a first catheter 54*a* and a second catheter 54*b*) are explained in the above examples, additional catheters 54 (within the heart and/or outside the heart) may be used to achieve the desired electric field gradient along the path within the region of tissue to be ablated.

In some instances, electrodes 56 located in non-targeted regions of the patient anatomy (e.g., regions outside of the heart that are not intended to be ablated, regions within the heart that are not intended to be ablated, etc.) may include low conductivity irrigants or less conductive materials such as conductive polymers or oxidized metals. Accordingly, such electrodes 56 may have an effect on the electric field gradient along the path within the region of tissue to be ablated while minimizing or avoiding ablation in the non-targeted regions. In some instances, each electrode 56 located in non-targeted regions of the patient anatomy may include a larger surface area than the electrodes 56 located in the targeted region in order to minimize or avoid ablation in the non-targeted regions. For example, the surface area of electrodes 56 in a respective non-targeted region and that receive a signal to affect the electric field gradient may be kept above a threshold surface area per energy level to attempt to minimize or avoid ablation in the non-targeted regions.

Figure 6:
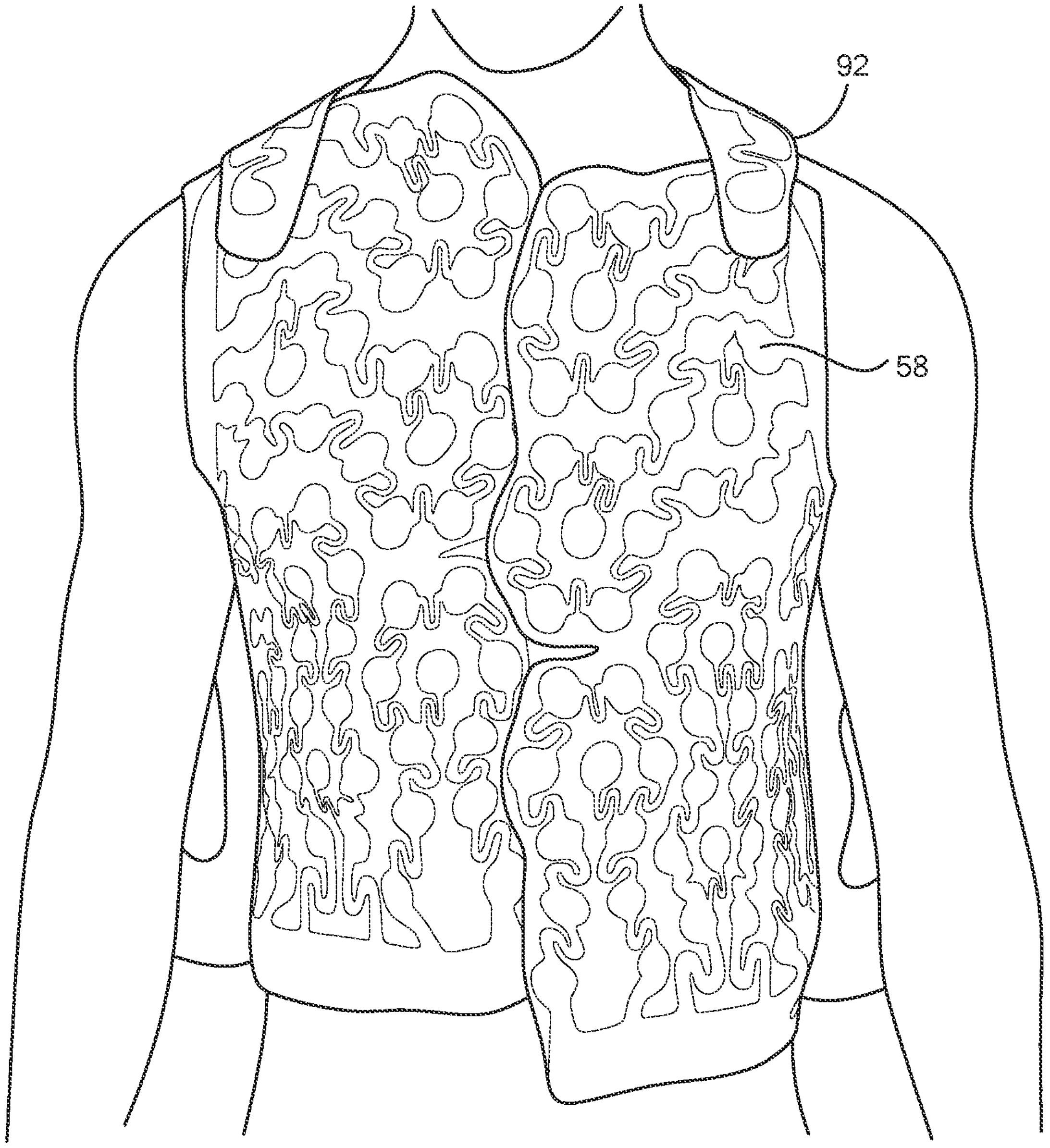
FIG. 6 illustrates a vest with external electrodes.

FIG. 6 illustrates a vest 92 that may be worn by the patient. The vest 92 provides external electrodes 58 located outside a body of the patient that may be used in conjunction with electrodes 56 within the patient such as the electrodes 56 of the catheters 54. The mapping and navigation system 28 may associate certain selected external electrodes 58 with certain selected internal electrodes 56 to achieve one or more desired electric field gradients within the patient's body. While the external electrodes 58 are shown as part of a vest 92, in some instances, the external electrodes 58 may not be part of the vest 92. For example, the external electrodes 58 may be part of a body surface patch that includes one or more electrodes 58 and that may be configured to be temporarily attached to an external surface of the body of the patient.

Figure 7:
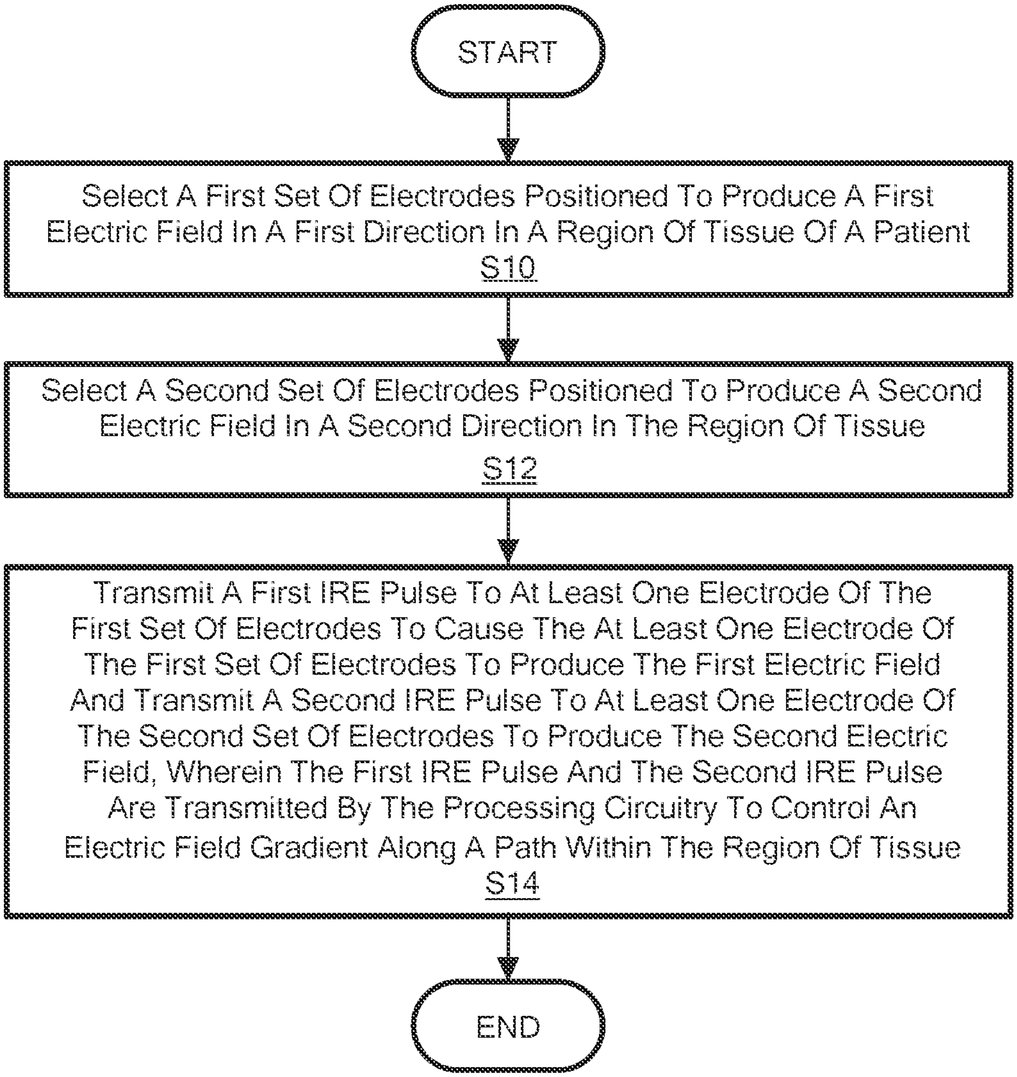
FIG. 7 is a flowchart of one example process in an IRE system according to principles disclosed herein.

FIG. 7 is a flowchart of one example process that may be implemented by the processing circuitry 48. The process may include selecting a first set of electrodes 56*a* positioned to produce a first electric field in a first direction in a region of tissue of a patient (Block S10). The process may also include selecting a second set of electrodes 56*b* positioned to produce a second electric field in a second direction in the region of tissue (Block S12). In some instances, the processing circuitry 48 may select one or both of the first set of electrodes 56 based on user inputs received from a user and/or based on desired known/stored values of desired ablation parameters for a given medical procedure as explained previously herein. The process may further include transmitting a first IRE pulse to at least one electrode 56 of the first set of electrodes 56*a* to cause the at least one electrode 56 of the first set of electrodes 56*a* to produce the first electric field and transmitting a second IRE pulse to at least one electrode 56 of the second set of electrodes 56*b* to cause the at least one electrode 56 of the second set of electrodes 56*b* to produce the second electric field (Block S14). The first IRE pulse and the second IRE pulse may be transmitted to respective electrodes 56*a*, 56*b* by the processing circuitry 48 (e.g., via pulse generator 50) to control an electric field gradient along a path within the region of tissue. The process of FIG. 7 may be performed by the processing circuitry 48 to control one or more electrodes 56 on one or more catheters 54 to provide test pulses and/or IRE pulses to specific tissue regions as explained herein.

Figure 8:
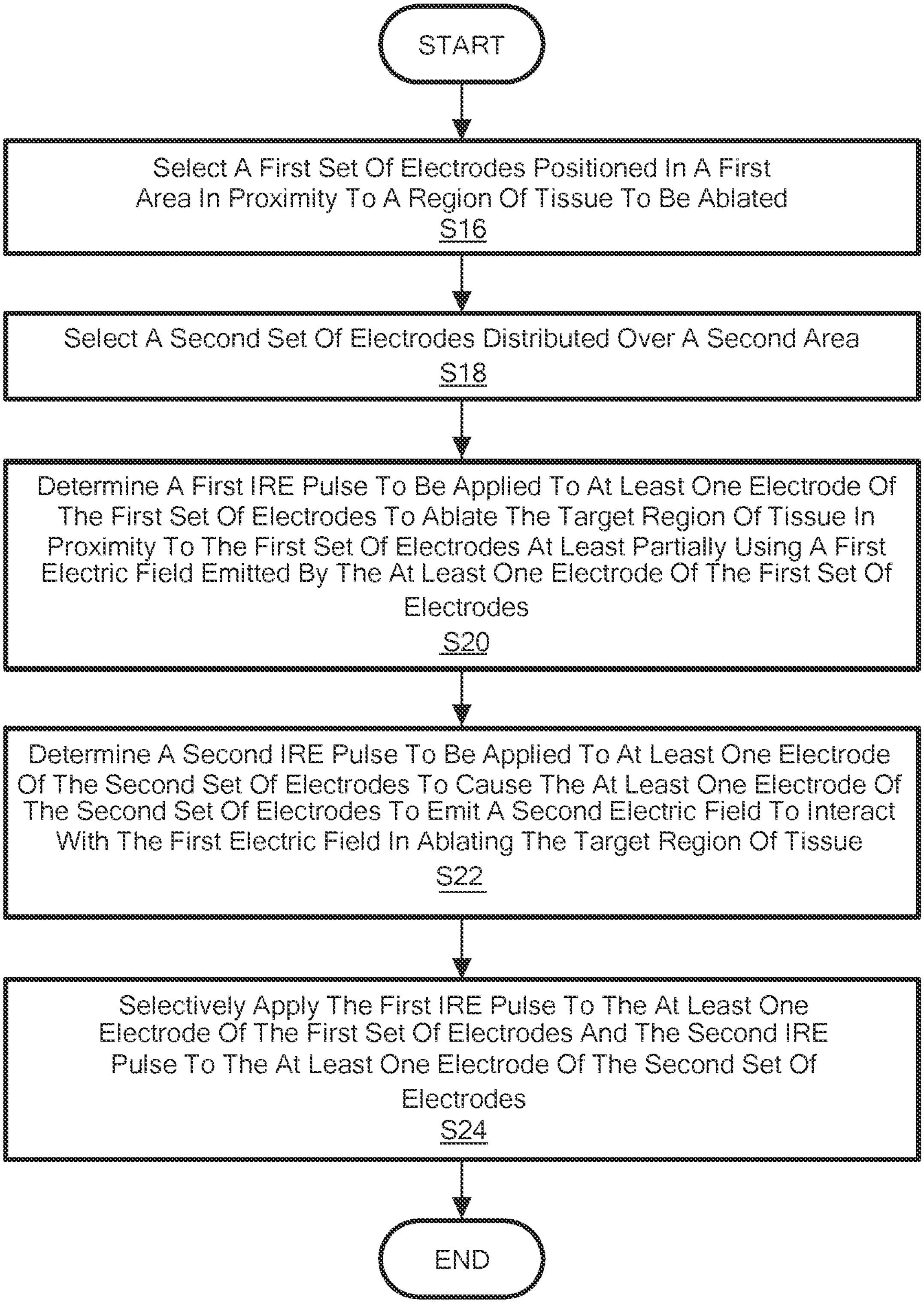
FIG. 8 is a flowchart of another example process in an IRE system according to principles disclosed herein.

FIG. 8 is a flowchart of another example process that may be implemented by the processing circuitry 48. The process may include selecting a first set of electrodes 56*a* positioned in a first area in proximity to a region of tissue to be ablated (Block S16). The process also may include selecting a second set of electrodes 56*b* distributed over a second area (Block S18). As indicated previously herein, the second area may also be near/in proximity to the region of tissue to be ablated. For example, the first area and the second area may both be within a heart of a patient. In other instances, the second area may not be near/in proximity to the region to be ablated. For example, the first area may be located in the heart while the second area may be located outside of the heart (e.g., in one of the locations shown in FIG. 5). The process may further include a first IRE pulse to be applied to at least one electrode 56 of the first set of electrodes 56*a* to ablate the target region of tissue in proximity to the first set of electrodes 56*a* at least partially using a first electric field emitted by the at least one electrode 56 of the first set of electrodes 56*a* (Block S20). The process may further include determining a second IRE pulse to be applied to at least one electrode 56 of the second set of electrodes 56*b* to cause the at least one electrode 56 of the second set of electrodes 56*b* to emit a second electric field to interact with the first electric field in ablating the target region of tissue (Block S22). The process may further include selectively applying the first IRE pulse to the at least one electrode 56 of the first set of electrodes 56*a* and the second IRE pulse to the at least one electrode 56 of the second set of electrodes 56*b* (Block S24). The processing circuitry 48 may perform any one or combination of the blocks S16-S24 based on user inputs received from a user and/or based on desired known/stored values of desired ablation parameters for a given medical procedure as explained previously herein. The process of FIG. 8 may be performed by the processing circuitry 48 to control one or more electrodes 56 on one or more catheters 54 to provide test pulses and/or IRE pulses to specific tissue regions as explained herein.

According to one aspect, the IRE system 46 includes processing circuitry 48 configured to: select a first set of electrodes 56*a* positioned to produce a first electric field in a first direction in a region of tissue of a patient. The processing circuitry 48 is also configured to select a second set of electrodes 56*b* positioned to produce an second electric field in a second direction in the region of tissue, the first direction being one of orthogonal to and at an acute angle to the second direction. The processing circuitry 48 may be further configured to direct a least one IRE pulse to at least one electrode 56*a* of the first set of electrodes 56*a* and to direct at least one IRE pulse to at least one electrode 56*b* of the second set of electrodes 56*b* to control at least one electric field gradient along a path inside the region of tissue.

In one aspect, the present disclosure provides an irreversible electroporation (IRE) system. According to one aspect, the IRE system includes processing circuitry that may be configured to select a first set of electrodes positioned to produce a first electric field in a first direction in a region of tissue of a patient, and select a second set of electrodes positioned to produce a second electric field in a second direction in the region of tissue. The processing circuitry may also be configured to transmit a first IRE pulse to at least one electrode of the first set of electrodes to cause the at least one electrode of the first set of electrodes to produce the first electric field and transmit a second IRE pulse to at least one electrode of the second set of electrodes to cause the at least one electrode of the second set of electrodes to produce the second electric field. The first IRE pulse and the second IRE pulse may be transmitted by the processing circuitry to control an electric field gradient along a path within the region of tissue.

In addition to any combination of features described above, the first IRE pulse may be different than the second IRE pulse such that the first electric field has a different level of strength than the second electric field.

In addition to any combination of features described above, the processing circuitry may be configured to transmit a non-IRE test pulse to at least one of the group consisting of the first set of electrodes, the second set of electrodes, and a third set of electrodes to cause the at least one of the group consisting of the first set of electrodes, the second set of electrodes, and the third set of electrodes to generate a third electric field. The processing circuitry mal also be configured to receive, from at least one of the group consisting of the first set of electrodes, the second set of electrodes, the third set of electrodes, and a fourth set of electrodes, electrical signals indicative of the third electric field. The processing circuitry may also be configured to map electrical activity within the region of tissue based on the electrical signals indicative of the third electric field.

In addition to any combination of features described above, at least one electrode of the at least one of the group consisting of the first set of electrodes, the second set of electrodes, the third set of electrodes, and the fourth set of electrodes may be located external to the patient.

In addition to any combination of features described above, the processing circuitry may be configured to transmit the non-IRE test pulse, receive the electrical signals, and map the electrical activity at one or both of a time before and a time after an ablation procedure is performed on at least part of the region of tissue.

In addition to any combination of features described above, the IRS system may include a graphical user interface that includes a video display configured to receive and display a map of the electrical activity within the region of tissue onto a rendering of a patient anatomy that includes the region of tissue.

In addition to any combination of features described above, a first catheter may include the first set of electrodes and the second set of electrodes. Alternatively, a first catheter may include the first set of electrodes, and a second catheter may include the second set of electrodes.

In addition to any combination of features described above, the first catheter may be positioned in a first chamber of a heart of the patient, and the second catheter may be positioned in a second chamber of the heart of the patient.

In addition to any combination of features described above, the first catheter may be positioned in a chamber of a heart of the patient, and the second catheter may be positioned outside of the heart of the patient and in one of a pericardial space of the patient, an esophagus of the patient, and a substernal space of the patient.

In addition to any combination of features described above, the processing circuitry may be configured to control the first IRE pulse and the second IRE pulse to cause the electric field gradient to reach a target electric field gradient. The target electric field gradient may correspond to an electric field strength above a threshold throughout the region of tissue.

In addition to any combination of features described above, the first direction, the second direction, or both the first direction and the second direction may be selected to align with a polarization direction associated with polarizable cells of the region of tissue.

In addition to any combination of features described above, a first catheter may include the first set of electrodes, and the second set of electrodes may include an external electrode located outside of a body of the patient.

According to another aspect, an IRE system includes processing circuitry that may be configured to select a first set of electrodes positioned in a first area in proximity to a target region of tissue to be ablated, and select a second set of electrodes distributed over a second area. The processing circuitry may also be configured to determine a first IRE pulse to be applied to at least one electrode of the first set of electrodes to ablate the target region of tissue in proximity to the first set of electrodes at least partially using a first electric field emitted by the at least one electrode of the first set of electrodes. The processing circuitry may also be configured to determine a second IRE pulse to be applied to at least one electrode of the second set of electrodes to cause the at least one electrode of the second set of electrodes to emit a second electric field to interact with the first electric field in ablating the target region of tissue. The processing circuitry may also be configured to selectively apply the first IRE pulse to the at least one electrode of the first set of electrodes and the second IRE pulse to the at least one electrode of the second set of electrodes.

In addition to any combination of features described above, the processing circuitry may also be configured to adjust an impedance for each electrode of the at least one electrode of the first set of electrodes and each electrode of the at least one electrode of the second set of electrodes. The impedance may be adjusted by the processing circuitry based on a desired current for each electrode.

In addition to any combination of features described above, the desired current may be selected to be below an overcurrent condition threshold. The processing circuitry may also be configured to select the impedance for a first electrode to avoid an overcurrent condition for an IRE pulse determined to be provided to the first electrode.

In addition to any combination of features described above, the processing circuitry may also be configured to determine a target electric field gradient to provide an electric field strength above a threshold throughout a specified volume of the target region of tissue. The processing circuitry may also be configured to select the first set of electrodes and the second set of electrodes and selectively apply the first IRE pulse and the second IRE pulse to cause an electric field gradient throughout the specified volume of the target region of tissue to reach the target electric field gradient.

In addition to any combination of features described above, the at least one electrode of the second set of electrodes may be positioned with respect to a position of the at least one electrode of the first set of electrodes in order to produce a combined electric field in a direction aligned with a polarization direction associated with polarizable cells of the target region of tissue. The combined electric field may be produced by a combination of the first electric field and the second electric field.

In addition to any combination of features described above, the processing circuitry may also be configured to transmit a non-IRE test pulse to at least one of the group consisting of the first set of electrodes, the second set of electrodes, and a third set of electrodes. The processing circuitry may also be configured to receive electrical signals responsive to the non-IRE test pulse from at least one of the group consisting of the first set of electrodes, the second set of electrodes, the third set of electrodes, and a fourth set of electrodes. The processing circuitry may also be configured to map the electrical signals onto a rendering of a patient anatomy that includes the target region of tissue that is displayable on a video monitor.

In addition to any combination of features described above, the processing circuitry may also be configured to transmit the non-IRE test pulse, and receive and map the electrical signals, after the target region of tissue is at least partially ablated.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more electronic processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings.

What is claimed is:

1. An irreversible electroporation (IRE) system, the IRE system comprising:

processing circuitry configured to:

receive, via a user interface, a user input that indicates a target location of an anatomy of a patient to be ablated;

determine a respective position of each electrode of a plurality of electrodes with respect to the anatomy of the patient;

select, based on the target location and based on the respective positions of the plurality of electrodes, a first set of electrodes positioned to produce a first electric field in a first direction at the target location;

select, based on the target location and based on the respective positions of the plurality of electrodes, a second set of electrodes positioned to produce a second electric field in a second direction at the target location; and transmit a first IRE pulse to at least one electrode of the first set of electrodes to cause the at least one electrode of the first set of electrodes to produce the first electric field and transmit a second IRE pulse to at least one electrode of the second set of electrodes to cause the at least one electrode of the second set of electrodes to produce the second electric field, wherein the first IRE pulse and the second IRE pulse are transmitted by the processing circuitry to control an electric field gradient along a path within the target location.

2. The IRE system of claim 1, wherein the first IRE pulse is different than the second IRE pulse such that the first electric field has a different level of strength than the second electric field.

3. The IRE system of claim 1, wherein the processing circuitry is further configured to:

transmit a non-IRE test pulse to at least one of the group consisting of the first set of electrodes, the second set of electrodes, and a third set of electrodes to cause the at least one of the group consisting of the first set of electrodes, the second set of electrodes, and the third set of electrodes to generate a third electric field;

receive, from at least one of the group consisting of the first set of electrodes, the second set of electrodes, the third set of electrodes, and a fourth set of electrodes, electrical signals indicative of the third electric field; and map electrical activity within the target location based on the electrical signals indicative of the third electric field.

4. The IRE system of claim 3, wherein at least one electrode of the at least one of the group consisting of the first set of electrodes, the second set of electrodes, the third set of electrodes, and the fourth set of electrodes is located external to the patient.

5. The IRE system of claim 3, wherein the processing circuitry is configured to transmit the non-IRE test pulse, receive the electrical signals, and map the electrical activity at one or both of a time before and a time after an ablation procedure is performed on at least part of the target location.

6. The IRE system of claim 3, wherein the user interface includes a video display configured to receive and display a map of the electrical activity within the target location onto a rendering of the anatomy of the patient that includes the target location.

7. The IRE system of claim 1, wherein a first catheter includes the first set of electrodes and the second set of electrodes.

8. The IRE system of claim 1, wherein a first catheter includes the first set of electrodes and a second catheter includes the second set of electrodes.

9. The IRE system of claim 8, wherein the first catheter is configured to be positioned in a first chamber of a heart of the patient and the second catheter is configured to be positioned in a second chamber of the heart of the patient.

10. The IRE system of claim 8, wherein the first catheter is configured to be positioned in a chamber of a heart of the patient and the second catheter is configured to be positioned outside of the heart of the patient and in one of a pericardial space of the patient, an esophagus of the patient, and a substernal space of the patient.

11. The IRE system of claim 1, wherein the processing circuitry is configured to control the first IRE pulse and the second IRE pulse to cause the electric field gradient to reach a target electric field gradient, wherein the target electric field gradient corresponds to an electric field strength above a threshold throughout the target location.

12. The IRE system of claim 1, wherein the first direction, the second direction, or both the first direction and the second direction are selected to align with a polarization direction associated with polarizable cells of the target location.

13. The IRE system of claim 1, wherein a first catheter includes the first set of electrodes, and wherein the second set of electrodes includes an external electrode located outside of a body of the patient.

14. An irreversible electroporation (IRE) system, the IRE system comprising:

processing circuitry configured to:

receive, via a user interface, a user input that indicates a target location of an anatomy of a patient to be ablated;

determine a respective position of each electrode of a plurality of electrodes with respect to the anatomy of the patient;

select, based on the target location and based on the respective positions of the plurality of electrodes, a first set of electrodes positioned in a first area in proximity to the target location;

select, based on the target location and based on the respective positions of the plurality of electrodes, a second set of electrodes distributed over a second area;

determine a first IRE pulse to be applied to at least one electrode of the first set of electrodes to ablate the target location in proximity to the first set of electrodes at least partially using a first electric field emitted by the at least one electrode of the first set of electrodes;

determine a second IRE pulse to be applied to at least one electrode of the second set of electrodes to cause the at least one electrode of the second set of electrodes to emit a second electric field to interact with the first electric field in ablating the target location; and selectively apply the first IRE pulse to the at least one electrode of the first set of electrodes and the second IRE pulse to the at least one electrode of the second set of electrodes.

15. The IRE system of claim 14, wherein the processing circuitry is further configured to adjust an impedance for each electrode of the at least one electrode of the first set of electrodes and each electrode of the at least one electrode of the second set of electrodes, the impedance being adjusted based on a desired current for each electrode.

16. The IRE system of claim 15, wherein the desired current is selected to be below an overcurrent condition threshold, and wherein the processing circuitry is further configured to select the impedance for one or more electrodes (i) of the at least one electrode of the first set of electrodes, (ii) of the at least one electrode of the second set of electrodes, or (iii) of the at least one electrode of the first set of electrodes and of the at least one electrode of the second set of electrodes to avoid an overcurrent condition for an IRE pulse determined to be provided to the first electrode.

17. The IRE system of claim 14, wherein the processing circuitry is further configured to determine a target electric field gradient to provide an electric field strength above a threshold throughout a specified volume of the target location; and wherein the processing circuitry is configured to select the first set of electrodes and the second set of electrodes and selectively apply the first IRE pulse and the second IRE pulse to cause an electric field gradient throughout the specified volume of the target location to reach the target electric field gradient.

18. The IRE system of claim 14, wherein the at least one electrode of the second set of electrodes is positioned with respect to a position of the at least one electrode of the first set of electrodes in order to produce a combined electric field in a direction aligned with a polarization direction associated with polarizable cells of the target location, wherein the combined electric field is produced by a combination of the first electric field and the second electric field.

19. The IRE system of claim 14, wherein the processing circuitry is further configured to:

transmit a non-IRE test pulse to at least one of the group consisting of the first set of electrodes, the second set of electrodes, and a third set of electrodes;

receive electrical signals responsive to the non-IRE test pulse from at least one of the group consisting of the first set of electrodes, the second set of electrodes, the third set of electrodes, and a fourth set of electrodes; and map the electrical signals onto a rendering of the anatomy of the patient that includes the target location that is displayable on a video monitor of the user interface.

20. The IRE system of claim 19, wherein the processing circuitry is configured to transmit the non-IRE test pulse, and receive and map the electrical signals, after the target location is at least partially ablated.

* * * * *